(12) United States Patent
Zhang et al.

(10) Patent No.: US 12,419,617 B2
(45) Date of Patent: Sep. 23, 2025

(54) DEVICE AND SYNCHRONOUS METHOD FOR SUPPLYING POWER TO AN ULTRASOUND TRANSDUCER

(71) Applicants: UNIVERSITE PARIS-SACLAY, Gif-sur-Yvette (FR); CENTRE NATIONAL DE LA RECHERCHE SCIENTIFIQUE, Paris (FR)

(72) Inventors: Ming Zhang, Fontenay-sous-Bois (FR); Nicolas Llaser, Fontenay-sous-Bois (FR)

(73) Assignees: UNIVERSITE PARIS-SACLAY, Gif-sur-Yvette (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 105 days.

(21) Appl. No.: 18/017,514

(22) PCT Filed: Jul. 30, 2021

(86) PCT No.: PCT/EP2021/071505
§ 371 (c)(1),
(2) Date: Jan. 23, 2023

(87) PCT Pub. No.: WO2022/023577
PCT Pub. Date: Feb. 3, 2022

(65) Prior Publication Data
US 2024/0260947 A1 Aug. 8, 2024

(30) Foreign Application Priority Data
Jul. 30, 2020 (FR) .................. FR2008137

(51) Int. Cl.
*B06B 1/02* (2006.01)
*A61B 8/00* (2006.01)
*G01S 7/52* (2006.01)

(52) U.S. Cl.
CPC .............. *A61B 8/56* (2013.01); *A61B 8/4488* (2013.01); *B06B 1/0223* (2013.01); *G01S 7/52096* (2013.01)

(58) Field of Classification Search
CPC . B06B 1/0223; B06B 1/0253; B06B 2201/76; H03F 3/68; H03F 3/187;
(Continued)

(56) References Cited

U.S. PATENT DOCUMENTS 11,273,331 B2 * 3/2022 Jang ................ A61B 8/085
11,464,497 B2 * 10/2022 Taffler ................ A61B 8/565
(Continued)

FOREIGN PATENT DOCUMENTS

| CN | 201226589 Y | 4/2009 |
| JP | 2013533759 A | 8/2013 |
| WO | 2011154782 A1 | 12/2011 |

OTHER PUBLICATIONS

French Search Report dated Apr. 6, 2021, in corresponding French Application No. 2008137, 7 pages.
(Continued)

*Primary Examiner* — Daniel L Murphy
*Assistant Examiner* — Amie M Ndure
(74) *Attorney, Agent, or Firm* — Maier & Maier, PLLC

(57) ABSTRACT

A method and circuit for driving and supplying power to ultrasonic transducers with synchronous switched capacity, controlled by digital loop. This circuit includes a power interface controlled by a multi-level square or rectangular signal generator. This device includes a tuning circuit which is controlled by a tuning control circuit to have, with the transducer, a determined natural frequency. Typically, this tuning includes at the input an inductor in series, and at the output a controlled connection capacitor mounted in parallel with the transducer. This connection is controlled according (Continued)

to a detected phase difference detected between the input and the output of the inductor. It is advantageously controlled to provide a phase difference equal to $\pi/2$. Also, an ultrasonic element, an ultrasonic head, and an ultrasonic imaging and/or processing system, especially medical.

20 Claims, 3 Drawing Sheets

(58) Field of Classification Search
CPC .......... H03F 3/2175; H03F 3/2171; H03F 2200/391; H03F 2200/378; H03F 2200/261; H03F 2200/351; A61B 8/4488; A61B 8/56; A61B 8/00; G01S 7/52096
See application file for complete search history.

(56) References Cited

U.S. PATENT DOCUMENTS

| | | | |
|---|---|---|---|
| 2005/0131301 A1* | 6/2005 | Peszynski | A61B 8/14 600/459 |
| 2006/0184035 A1* | 8/2006 | Kimura | A61B 8/4488 600/466 |
| 2007/0071266 A1* | 3/2007 | Little | A61B 8/4444 381/328 |
| 2013/0241468 A1* | 9/2013 | Moshfeghi | H02J 50/05 320/107 |
| 2015/0018688 A1 | 1/2015 | Osawa et al. | |
| 2015/0080724 A1* | 3/2015 | Rothberg | G03B 27/52 600/440 |
| 2017/0290568 A1 | 10/2017 | Ko et al. | |
| 2018/0360420 A1 | 12/2018 | Vortman et al. | |
| 2018/0367111 A1* | 12/2018 | Singh | G01S 7/526 |
| 2019/0307427 A1 | 10/2019 | Levy et al. | |

OTHER PUBLICATIONS

International Search Report dated Nov. 11, 2021, in corresponding International Application No. PCT/EP2021/071505, 8 pages.
Zhang et al., "Measurement and auto-tuning of the resonance frequency of an ultrasonic transducer", HAL Id:hal-01280191, https://hal.archives-overtes.fr/hal-01280191, Jan. 20, 2016, XP055856843, 7 pages.
Wang et al., "Optimized Design of a Driver Circuit for an Ultrasound Transducer for Medical Applications", Instrumentation Mesure Metrologie, International Information and Engineering Technology Association, vol. 19, No. 3, Jun. 1, 2020, XP055856845, pp. 211-219.
Wang et al., "CMOS 0.35m implementation of an auto-tuning system for a resonant converter", Analog Integrated Circuits and Signal Processing, Springer New York LLC, vol. 89, No. 1, May 21, 2016, XP036053630, pp. 35-44.
Wang et al., "A simple structure AGC for synchronous capacitor resonant converter used in HIFU application", 2014, 21st IEEE International Conference on Electronics, Circuits and Systems (ICECS), IEEE, Dec. 7, 2014, XP032740095, pp. 474-477.
Wang et al., "Auto Tuning System for a Half Bridge Resonant Converter Using a Synchronous Switched Capacitor", 2015 IEEE 13th International New Circuits and Systems Conference (NEWCAS), IEEE, Jun. 7, 2015, XP033190676, 4 pages.
Office Action issued on May 28, 2024, in corresponding Japanese Application No. 2023-506192, 12 pages.

* cited by examiner

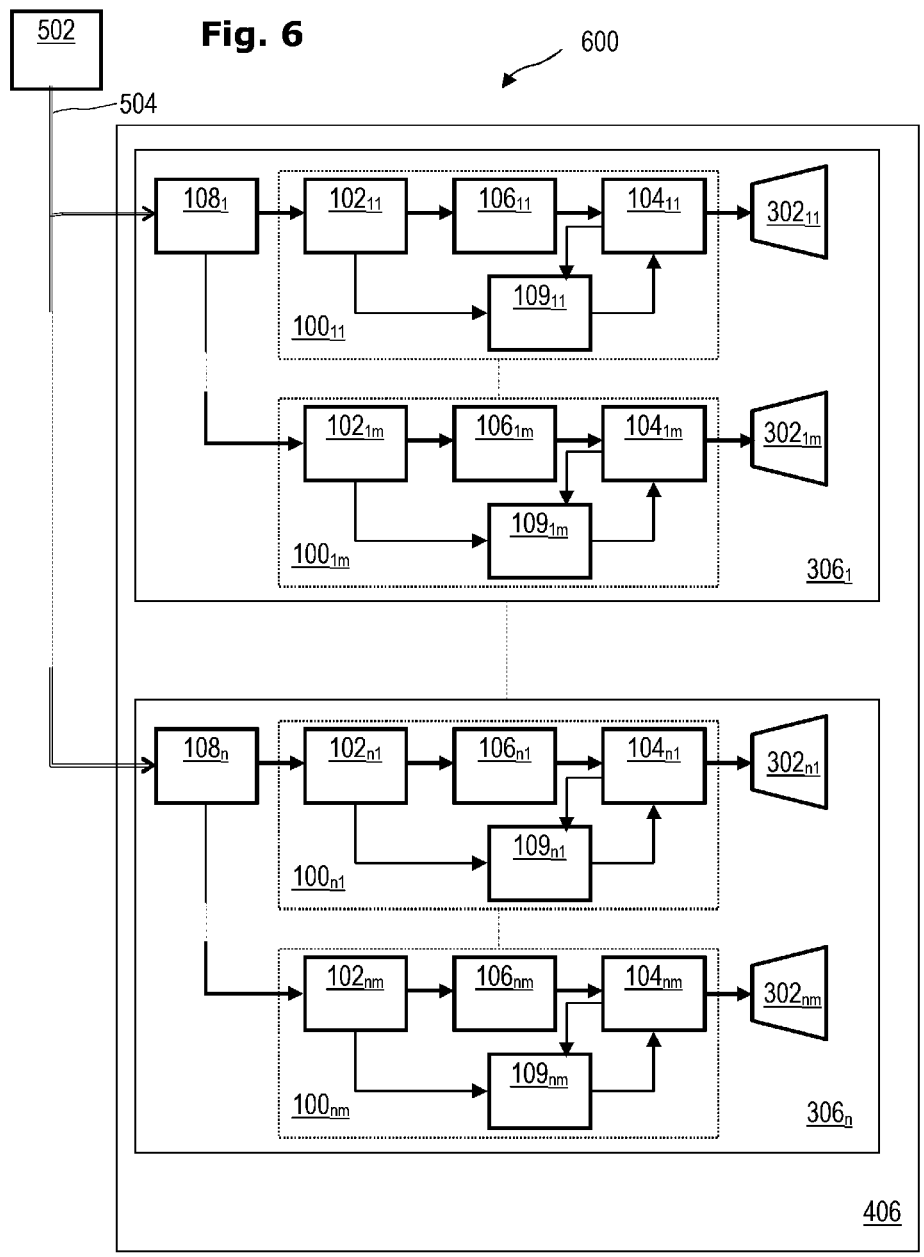

DEVICE AND SYNCHRONOUS METHOD FOR SUPPLYING POWER TO AN ULTRASOUND TRANSDUCER

FIELD

The invention relates to a method and circuit for driving and supplying ultrasonic transducers with synchronous switched capacity, controlled by digital loop. This circuit comprises a power interface controlled by a multi-level square or rectangular signal generator. This device comprises a tuning circuit which is controlled to have, with the transducer, a determined natural frequency.

Typically, this tuning circuit comprises at the input an inductor in series, and at the output a controlled connection capacitor mounted in parallel with the transducer. This connection is controlled according to a phase difference detected between the input and the output of said inductor. It is advantageously controlled to provide a phase difference equal to $\pi/2$.

The invention further relates to an ultrasonic element, an ultrasonic head, and an ultrasonic imaging and/or processing system, especially medical.

BACKGROUND

Ultrasonic transducers are widely used as emitters and receivers for imaging by echography, or even ultrasound treatment, in particular in the medical field. To do this, a plurality of transducers are typically arranged in a matrix, also called an "ultrasonic head", in order to emit focused, high-power ultrasound in the area to be imaged or processed. Each ultrasonic transducer is supplied with a sinusoidal signal at a given frequency so as to generate an ultrasonic signal of said frequency.

Generally, the ultrasonic head comprises, for each ultrasonic transducer, an individual control chain. This chain makes it possible to modify, individually for each transducer, the amplitude of the ultrasonic signal emitted by said transducer, as well as its frequency and phase. Thus, the characteristics of the ultrasonic wave transmitted by each transducer of the matrix can be modified.

However, known control chains for ultrasonic transducers have degraded efficiencies. Furthermore, the sinusoidal control signals provided by known control chains are of poor quality, causing the ultrasonic signal to be degraded. Finally, known control chains are generally bulky and energy-consuming.

One aim of the present invention is to overcome all or some of the drawbacks of the prior art, and in particular to at least one of the aforementioned drawbacks.

Another aim of the present invention is to propose a device for supplying power to an ultrasonic transducer that is more efficient in terms of efficiency.

Another aim of the present invention is to propose a device for supplying power to an ultrasonic transducer that provides a better-quality sinusoidal supply signal.

Another aim of the present invention is to propose a device for supplying power to an ultrasonic transducer that is less bulky, more energy-saving, and/or easier to manufacture in large quantities.

Another aim of the present invention is to propose a device for supplying power to an ultrasonic transducer enabling the modification of the power of the ultrasonic signal by modifying the amplitude of the signal supplied to each transducer.

Another aim of the present invention is to propose a device for supplying power to an ultrasonic transducer allowing the modification of the focal plane by modifying the frequency or the phase of the signal supplied to each transducer.

Another aim of the present invention is to make it possible to supply signals to a larger number of ultrasonic transducers in the ultrasonic head.

SUMMARY

For this, the invention proposes a device for supplying power to an ultrasonic transducer comprising a power interface configured to receive a drive signal, especially a multi-level square or rectangular signal provided by a multi-level square or rectangular signal generator controlled by a digital interface, and to provide an analog power signal, to said ultrasonic transducer so as to produce an ultrasonic wave of a setpoint frequency.

Typically, the power interface carries out an amplification of a multi-level square or rectangular signal generated by a digital square or rectangular multi-level signal generator, that amplification being carried out especially by means of a class "D" amplifier. Typically, the supply device comprises a digital interface that controls a multi-level square or rectangular signal generator, so that the latter generates a multi-level square or rectangular signal whose frequency, phase and amplitude respectively represent the frequency, phase, and amplitude of the ultrasonic wave to be transmitted.

According to the invention, the supply device further comprises a tuning circuit that is mounted between the interface and the ultrasonic transducer, which tuning circuit is controlled (preferably digitally) by a tuning control circuit, so that the assembly formed by the transducer and said tuning circuit has a determined resonant frequency, especially that is tuned to said setpoint frequency.

Typically, this impedance modification by means of a connectable or adjustable capacitor mounted in the tuning circuit, for example in parallel to the transducer. Typically, the tuning circuit also filters the harmonics of the analog power signal, for example by an inductor mounted in series, which is passed through by the analog power signal that supplies power to the transducer.

Preferably, the tuning circuit comprises an inductor mounted in series on the side of its input, and comprises on the side of its output a controlled connection capacitor mounted in parallel with the transducer.

This connection is controlled as a function of a detected phase difference detected between an input phase and an output phase, which are detected on the input side and on the side of the output of said inductor.

More particularly, the tuning circuit comprises a feedback circuit that is arranged to control the connection of the capacitor so as to ensure that the detected phase difference arrives at a determined setpoint value.

In a preferred embodiment, the feedback circuit comprises:
  a synchronization extraction circuit that detects the output phase,
  a phase comparator circuit, which receives or detects the input phase, especially before the input of the power interface and for example after the multi-level square or rectangular signal generator, and compares it with the output phase to pull the detected phase difference therefrom, a summing circuit that compares said detected phase difference with the setpoint value so as to control a correction circuit, and in that this correction circuit controls an output synchronization circuit, which controls in real time the opening and closing of the connection of the capacitor, in a controlled manner, in order to set and/or maintain the detected phase difference at the setpoint value.

Typically, this feedback circuit is entirely digital or almost so, aside from the synchronization extractor which is a mixed circuit.

According to an advantageous particular feature, the connection of the capacitor is controlled so that the detected phase difference arrives at a tuning value that is equal to $\pi/2$.

According to another particular feature, the connection of the capacitor is controlled by a synchronization signal operating in pulse width modulation (PWM).

Preferably, the supply device further comprises a digital control interface providing, in order to generate the drive signal, any combination of at least one of the following parameters:
a frequency of said drive signal,
an amplitude of said drive signal,
a phase of said drive signal;
and determining said parameters from instruction data that it receives and which respectively represent:
a frequency of a sound signal to be emitted by the transducer,
an amplitude of a sound signal to be emitted by the transducer,
a phase of a sound signal to be emitted by the transducer.

Potentially, several power supply devices are controlled by the same digital interface.

Advantageously, the tuning control circuit, and the control and generation circuits of the analog power signal at the input of the inductor, called the primary supply signal, are made entirely or partly by digital circuits.

Preferably, the supply device is integrated, partly or entirely, into at least one integrated circuit, especially alone or associated with other electronic components.

According to another aspect, the invention proposes an ultrasonic device that comprises at least:
an ultrasonic transducer, and
a supply device such as disclosed herein, which is arranged to supply signals to said at least one ultrasonic transducer.

According to a particular feature, such an ultrasonic device may comprise a single transducer and a single supply device, itself comprising its own digital interface According to another particular feature, several supply devices are controlled by the same digital interface, and the invention proposes a so-called composite ultrasonic device that comprises several ultrasonic devices that share a common digital interface.

According to yet another aspect, the invention proposes an ultrasonic head comprising several ultrasonic devices as set out here, which are arranged and/or controlled in parallel.

In the ultrasonic head according to the invention, each ultrasonic transducer is associated with a supply device dedicated to it such that each ultrasonic transducer can be individually controlled. Thus, the characteristics of the ultrasonic wave generated by each ultrasonic transducer of the ultrasonic head according to the invention can be modified individually.

In particular, the amplitude, frequency, and phase of the ultrasonic wave emitted by each ultrasonic transducer of the ultrasonic head can be modified for each ultrasonic transducer individually.

The ultrasonic head according to the invention can be used for medical imaging, in particular for ultrasound imaging.

Alternatively, or in addition, the ultrasonic head according to the invention can be used for medical therapy.

Alternatively, or in addition, the ultrasonic head according to the invention can be used for aesthetic treatment.

Alternatively, or in addition, the ultrasonic head according to the invention can be used for imaging workpieces, for example for the purpose of quality control, or even to process workpieces.

According to another aspect, the invention proposes an ultrasound system comprising:
an ultrasonic head as disclosed herein, and
at least one digital control apparatus for the ultrasonic devices of said ultrasonic head.

According to one embodiment, the ultrasound system according to the invention may comprise, for at least one, and in particular each, ultrasonic device of the ultrasonic head, an individual digital control apparatus dedicated to said ultrasonic device.

In this case, each ultrasonic device of the ultrasonic head receives the data concerning the ultrasonic wave to be generated from the digital control apparatus dedicated to it.

The system according to the invention may be an ultrasound imaging system. In this case, the system may comprise, in a known manner, means for processing ultrasound waves to generate at least one ultrasound image.

It may also be a treatment system. In this case, the system comprises, in a known manner, means for processing the emitted ultrasonic waves to carry out the treatment According to a particular preferred feature, the system is arranged to produce a medical imaging system, and/or a medical therapy system, for example for lysis of renal calculi.

According to another aspect of the invention, a use of the system according to the invention is proposed for medical imaging.

According to another aspect of the invention, a use of the system according to the invention is proposed, for the aesthetic treatment of at least one zone of the body of a human or animal.

According to yet another aspect, the invention proposes a method for supplying an ultrasonic transducer with a so-called secondary supply signal, to produce an ultrasonic wave of a setpoint frequency, characterized in that it comprises the following steps:
generating with a power interface an analog power signal so-called the primary supply signal used to supply an ultrasonic transducer through a tuning circuit with adjustable impedance, especially comprising a connectable or adjustable capacitance;
controlling a tuning circuit so that it controls said tuning circuit so as to modify the impedance thereof, so that the assembly formed by the transducer and said tuning circuit has a determined resonant frequency, especially which is tuned to said setpoint frequency.

Typically, this method is implemented within a power supply device, or an ultrasonic device, or an ultrasonic head, or an ultrasound system, as set forth herein.

According to one feature, the modification of the tuning of the tuning circuit is carried out by synchronous switching of a capacitor mounted in parallel with the transducer.

According to another particular feature, the switching of the capacitor and controlled by a feedback control relating to a detected phase difference detected between an input phase and an output phase, which are detected on the side of the input and on the side of the output of an inductor mounted in series between the power interface and the transducer.

The invention helps solve the problem of driving a matrix of transducers, in particular in an apparatus that must be compatible with MRI for medical treatments by ultrasound.

The invention makes it possible to implement a device that does not interfere with the magnetic field of the MRI and to enable individual control of the amplitude, frequency, and phase of the drive signal of each transducer. This individual control makes it possible to modify the focal point. This capacity for modifying the focal point makes it possible to follow moving members and to treat larger areas, thus facilitating the work of the physician. By virtue of its synchronous switching system based on synchronous switched capacitances, the invention makes it possible to offer a high energy conversion efficiency and at the same time to reduce the dimensions of the head and of the overall system, which makes it possible to increase the number of ultrasonic transmitting elements in a transducer array with all the resulting advantages.

Thus, the invention makes it possible to control each transducer independently and to control its amplitude, frequency and phase, in an MRI apparatus. Compared to existing solutions, this may enable finer control of the settings of each transducer. This will enable physicians to offer more precise processing operations and possibly new uses of this type of treatment. Several objectives are possible, such as the monitoring of moving members controlled by MRI or the treatment of larger areas in order to treat tumors of greater size.

The invention makes it possible to use an architecture mainly based on digital circuits, which makes the system more robust and simpler to develop and to implement. This may make it possible to reduce manufacturing costs compared with the analog solutions that are complex and difficult to adjust.

It makes possible in particular the following options:
Digital-first architecture: simple to implement, with cost reduction, high integration perspective and increased robustness
Individual control, for each transducer, of the amplitude, frequency and phase of the control signal
Automatic adjustment, or "autotuning", of the transducers, which allows the amplitude, frequency and phase to be set, enabling the physician to adjust the focal point, and also ensures the efficiency of the optimal energy conversion at any time.
Increasing the deflection of the ultrasonic signal, by adjusting the depth and the focal point, by virtue of the change of frequency and/or phase.
Improved precision of focusing.

Of course, the method according to the invention may comprise, in terms of method, any combination of at least one characteristic described above, which are not repeated here for the sake of conciseness.

Various embodiments of the invention are provided, incorporating, according to all of their possible combinations, the different optional features set out herein.

BRIEF DESCRIPTION OF THE DRAWINGS

Other features and advantages shall become evident from the detailed description of an entirely non-limiting embodiment, and from the enclosed drawings in which:

FIG. 6 is a schematic representation of a non-limiting embodiment of an ultrasound system according to the invention, including a variant of the head of FIG. 4 with composite subassemblies.

Figure 1:
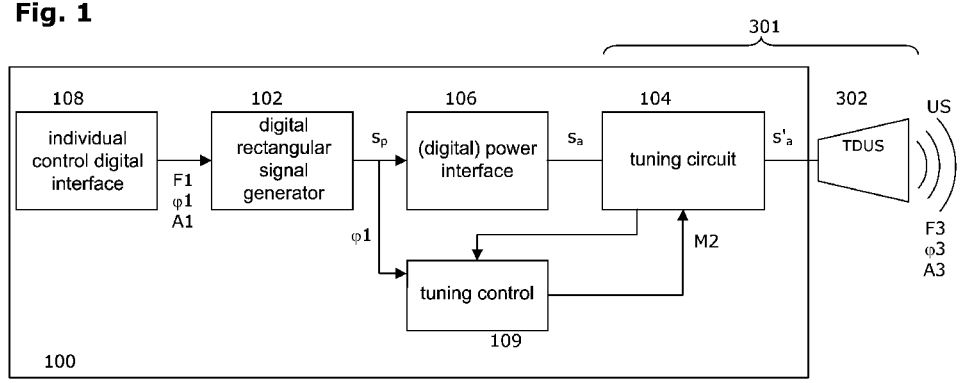
FIG. 1 is a schematic representation of a non-limiting embodiment of a power supply device of an ultrasonic transducer.
Figure 2:
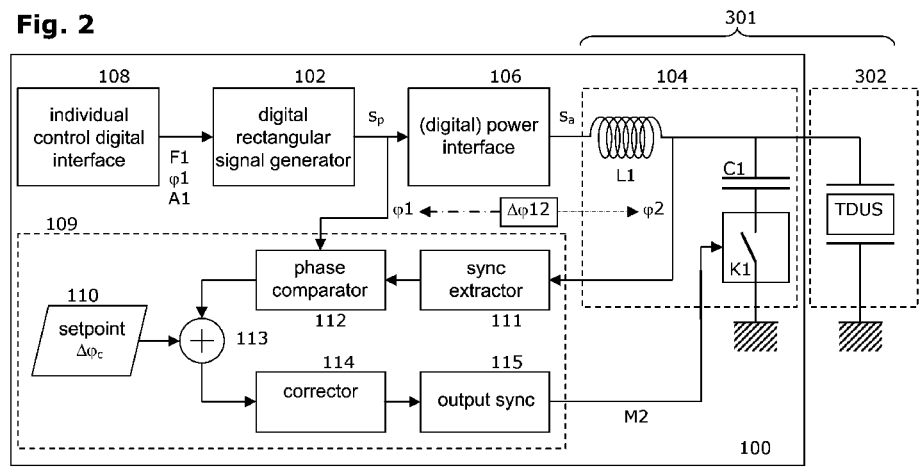
FIG. 2 is a more detailed embodiment of the power supply device of FIG. 1.

The embodiments that will be described hereafter are by no means limiting. It is especially possible to imagine variants of the invention that comprise only a selection of the features disclosed hereinafter in isolation from the other features disclosed, if this selection of features is sufficient to confer a technical benefit or to differentiate the invention with respect to the prior state of the art. This selection comprises at least one preferably functional feature that lacks structural details, or only has a portion of the structural details if that portion is sufficient on its own to confer a technical benefit or to differentiate the invention with respect to the prior state of the art.

In the figures the same reference has been used for the elements that are common to several figures.

DETAILED DESCRIPTION

The invention proposes a structure that makes it possible to control ultrasonic transducers, especially in the context of medical treatments.

The transducers $302_i$ are typically arranged as a matrix of n transducers, with "i" ranging from 1 to n.

Their combination makes it possible to emit high-power ultrasound, and which can be focused by emitting the different transducers simultaneously but with phases different from one another. In such an architecture, each transducer 302 has its own control interface and thus forms an ultrasound device 300 (also called ultrasonic device). These ultrasonic devices form individual ultrasonic elements within an assembly 400 that forms the ultrasonic (or ultrasound) head.

Within an operational ultrasound system 500, all the ultrasonic elements 300 are controlled by a digital system 502, generally a computer associated with a dialog interface, allowing the physician to set the power and the focal point of the ultrasound. These settings are translated by the digital system into individual control of each element of the ultrasound head, in amplitude, frequency and phase. Through a communication bus 504, each of these individual controls is sent to the digital interface 108 of the ultrasonic element 300 that corresponds thereto within the ultrasonic head 500.

For each ultrasonic element 300, this structure simultaneously carries out the control and the supply of the ultrasonic transducer 302 by an analog power signal "$s_a$", which can be qualified as the "primary" supply signal. This primary signal $s_a$ is generated by a power interface 106, which is controlled by a digital signal forming a drive signal "$s_p$", arising from a generator of square or rectangular multi-level rectangular signals 102.

Each of the generators of digital multi-level square signal or rectangular signals 102 is controlled in frequency "F1", in phase "φ1", or even in amplitude "A1", by means of the digital interface 108 corresponding thereto.

The power interface 106 is typically an "H" half-bridge, and/or a class "D" amplifier. Typically, it thus emits a primary multi-level square or rectangular supply signal of the same frequency F1 and of the same phase φ1.

The ultrasonic transducer 302 is in series with an inductor L1, which makes it possible to filter the harmonics of the multi-level square or rectangular signal and which supplies a sinusoidal signal "$s'_a$" to the terminals of the transducer 302, which can be qualified as a "secondary" supply signal. A capacitor C1 is placed in parallel with the transducer 302 using the electronic switch K1. By switching the capacitor C1 during only a determined part of the time, typically during a determined part of each period of the primary signal $s_a$ exiting from the power interface 106, a modification of the impedance of the tuning circuit 104 is obtained, which makes it possible to displace the resonance point (that is to say its resonance frequency F30) of the assembly 301 formed by the inductor L1, the capacitor C1 and the transducer 302, an assembly that can be described as a "tuned transducer" 301.

It should be noted that the multi-level square or rectangular signal generator 102, the phase comparator 112, the setpoint 110 and its summer 113, the corrector 114 and the output synchronization stage 115 are preferably entirely produced by digital circuits.

Figure 3:
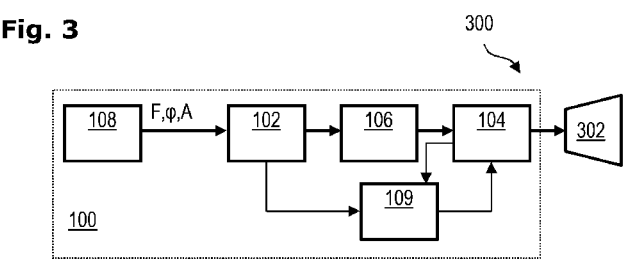
FIG. 3 is a schematic representation of a non-limiting embodiment of an ultrasonic device according to the invention, including the supply device of FIG. 1.

FIG. 3 is a schematic depiction of a non-limiting exemplary embodiment of an ultrasonic device according to the invention. The ultrasonic device 300 shown in FIG. 3 comprises an ultrasonic transducer 302 powered by a supply device according to the invention, and in particular the supply device 100 of FIG. 1.

Figure 4:
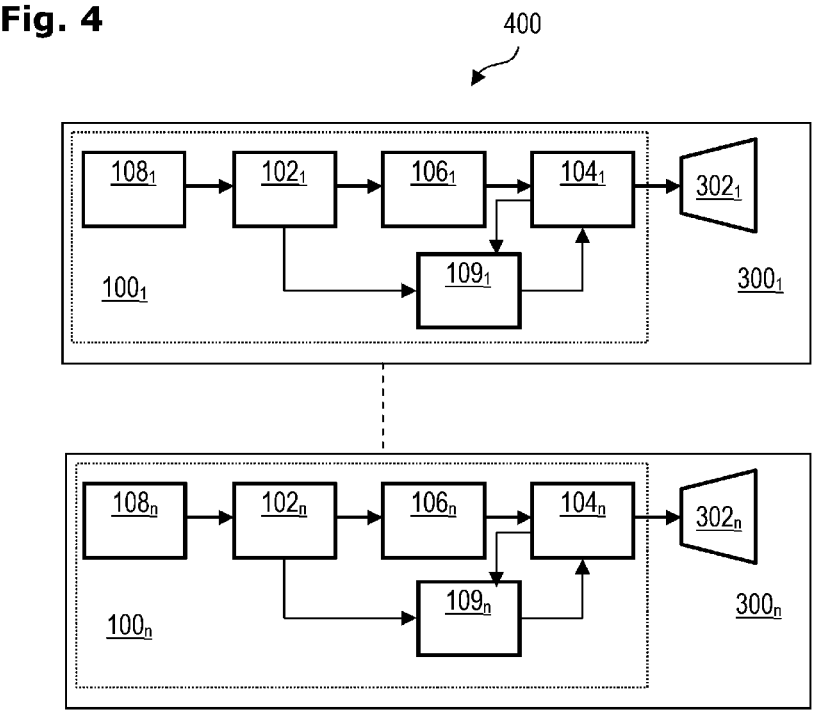
FIG. 4 is a schematic representation of a non-limiting embodiment of an ultrasonic head according to the invention, including an exemplary "n" matrix of the device of FIG. 3.

FIG. 4 is a schematic depiction of a non-limiting exemplary embodiment of an ultrasonic device according to the invention. The ultrasonic head 400 of FIG. 4 comprises "n" ultrasonic devices $300_1$-$300_n$ arranged in parallel and forming a matrix.

At least two of the ultrasonic devices $300_1$-$300_n$ may be the same or different from each other.

Each ultrasonic device $300_i$ may be identical to the ultrasonic device 300 of FIG. 3 and comprises all the elements of the device 300 with the same references that end with subscript "i".

Figure 5:
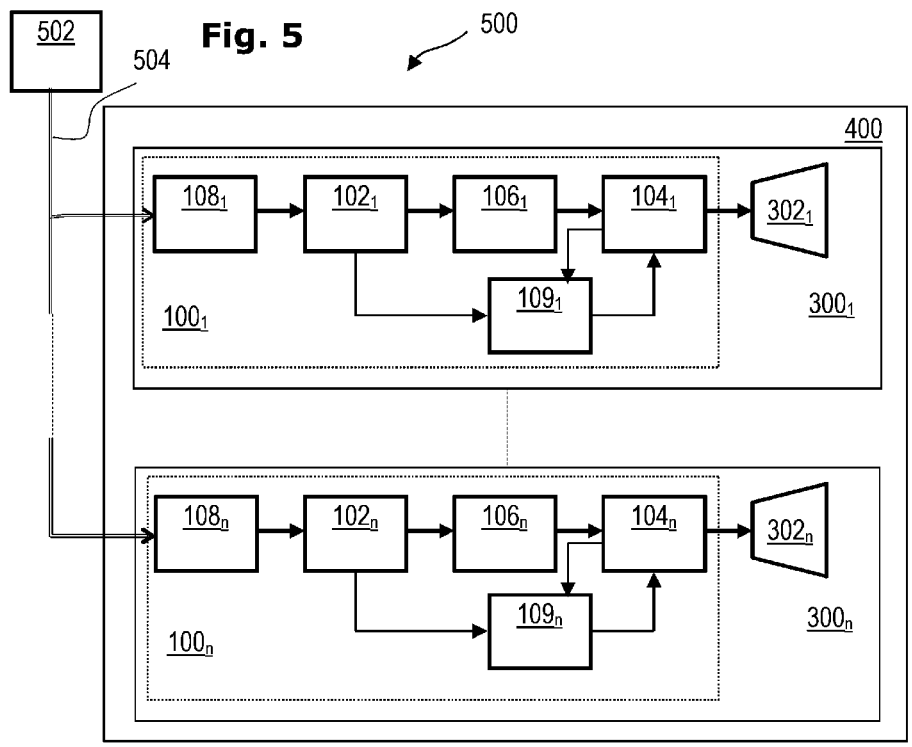
FIG. 5 is a schematic representation of a non-limiting embodiment of an ultrasound system according to the invention, including the head of FIG. 4.

FIG. 5 is a schematic depiction of a non-limiting exemplary embodiment of an ultrasound system according to the invention.

The ultrasound system 500 of FIG. 5 comprises an ultrasonic head according to the invention, such as for example the ultrasonic head 400 of FIG. 4.

The ultrasound system 500 further comprises a control apparatus 502, such as a computer or a tablet, and more generally any computer apparatus, connected to each ultrasonic device $300_i$ from the ultrasonic head 400, and in particular to the control interface $108_i$ of said ultrasonic device.

In the example shown, the control apparatus 502 is connected to each control interface $108_i$ through a digital 504 and wired 504 communication. Alternatively and by way of example, each control interface $108_i$, or only some of them, may be in communication with the control apparatus 502 through a wireless link.

The control apparatus 502 makes it possible to control each ultrasonic device $300_i$ individually and independently of the other ultrasonic devices $300_i$ in order to change the frequency, phase and/or amplitude of the ultrasonic wave emitted by each ultrasonic device $300_i$. This makes it possible to adjust, in a simple, dynamic, and responsive manner, the amplitude, frequency, and phase of each ultrasonic wave transmitted by each ultrasonic device $300_i$. Consequently, it is possible to simply, flexibly, and responsively adjust the focal point, typically by controlling, for the different elements $300_i$, phases that are different but coordinated with one another, as well as the amplitude of the ultrasonic waves emitted by the ultrasonic devices $300_1$-$300_n$.

For example, when the invention is implemented in a medical imaging device, or even therapy, it is thus possible to rapidly and accurately modify the focal point of the waves of the head 400, for example to perform real-time monitoring of the moving members.

FIG. 6 illustrates a variant of FIG. 5, in which the system 600 has a head 406 composed of a plurality of 'n' ultrasonic composite devices $306_1$ to $306_n$. Within each of these composite ultrasonic devices, for example the one referenced $306_{11}$, a same common interface $108_1$ controls a plurality of 'm' supply devices $100_{11}$ to $100_{1m}$, which each supply power to one single transducer $302_{11}$ to $302_{1m}$. In the same way, block $306_n$ comprises a single digital interface $108_n$ that directly controls the supply devices $100_{n1}$ to $100_{nm}$ transducers respectively $302_{n1}$ to $302_{nm}$.

This makes it possible to produce a digital interface block $108_1$ to $108_m$, each of which is capable of directly controlling a group of 'm' transducers of the matrix.

The matrix then consists of n·m transducers, which are associated in 'n' groups of 'm' transducers. This number 'm' is not necessarily constant, and can be variable within one subset to the other within the head. In general, this grouping of transducers is small, for example from 2 to 16.

Thus, it is for example possible to increase compactness and number of components in the digital interfaces within the head. It is also possible to produce in an industrial manner a compact, standard subassembly including a digital interface and 'm' transducers, that standard sub-assembly 306 potentially being used in different configurations to produce different types of heads.

Of course, the invention is not limited to the examples just described, and many adjustments can be made to these examples without going beyond the scope of the invention.

The invention claimed is:

1. An ultrasonic head comprising several ultrasonic devices, characterized in that each of said ultrasonic devices comprises an ultrasonic transducer and a supplying device to individually supply power to the ultrasonic transducer of said ultrasonic device, for each of said ultrasonic devices, the supplying device comprises a power interface configured to receive a drive signal, and to provide an analog power signal to said ultrasonic transducer so as to produce an ultrasonic wave of a setpoint frequency, for each of said ultrasonic devices, the supplying device comprises a tuning circuit that is mounted between the power interface and the ultrasonic transducer of said ultrasonic device, which tuning circuit is controlled by a tuning control circuit, wherein the assembly formed by the transducer and said tuning circuit has a determined resonant frequency.

2. The ultrasonic head according to claim 1, wherein, for each of said ultrasonic devices, the tuning circuit comprises an inductor mounted in series on the side of its input, and comprises on the side of its output a controlled connection capacitor mounted in parallel with the transducer, which connection is controlled as a function of a detected phase difference detected between an input phase and an output phase, which are detected on the input side and respectively on the side of the output of said inductor.

3. The ultrasonic head according to claim 2, wherein, for each of said ultrasonic devices, the tuning circuit comprises a feedback circuit which is arranged to control the connection of the capacitor so as to ensure that the detected phase difference arrives at a determined setpoint value.

4. The ultrasonic head according to claim 3, wherein, for each of said ultrasonic devices, control of the connection of the capacitor is configured to cause the detected phase difference to arrive at a tuning value that is equal to $\pi/2$.

5. The ultrasonic head according to claim 2, wherein, for each of said ultrasonic devices, the connection of the capacitor is controlled by a synchronization signal operating in pulse width modulation.

6. The ultrasonic head according to claim 1, further comprising, for each of said ultrasonic devices, a digital control interface providing, for generating the drive signal, any combination of at least one of the following parameters:
a frequency of said drive signal,
an amplitude of said drive signal,
a phase of said drive signal;
and determining said parameters from instruction data that it receives and which respectively represent:
a frequency of a sound signal to be emitted by the transducer,
an amplitude of a sound signal to be emitted by the transducer,
a phase of a sound signal to be emitted by the transducer.

7. The ultrasonic head according to claim 1, wherein, for each of said ultrasonic devices, the tuning control circuit, and the control and generation circuits of the analog power signal at the input of the inductor, so-called primary supply signal, are carried out wholly or partly by digital circuits.

8. The ultrasonic head according to claim 1, wherein, for each of said ultrasonic devices, the device is integrated, partly or entirely, into at least one integrated circuit.

9. The ultrasonic head according to claim 8, wherein integration of the device into the at least one integrated circuit is one of: alone, or with an association between the device and other electronic components of the integrated circuit.

10. The ultrasonic head according to claim 1, wherein said ultrasonic devices are arranged and/or controlled in parallel.

11. The ultrasonic head according to claim 1, wherein the drive signal is one of a multi-level square or rectangular signal provided by a multi-level square or rectangular signal generator controlled by a digital interface.

12. The ultrasonic head according to claim 1, wherein the determined resonant frequency is tuned to the setpoint frequency.

13. An ultrasonic system comprising:
the ultrasonic head according to claim 1, and
at least one digital control apparatus for the ultrasonic devices of said ultrasonic head.

14. The system according to claim 13, wherein the system is arranged to produce a medical imaging and/or therapy system.

15. A method for supplying power to an ultrasonic transducer of an ultrasonic device of an ultrasonic head according to claim 1, with a secondary power supply signal, to produce an ultrasonic wave of a setpoint frequency, said method comprising the following steps:
generating with a power interface an analog power signal primary power supply signal used to power an ultrasonic transducer through a tuning circuit with adjustable impedance; and
controlling a tuning circuit so that it controls said tuning circuit so as to modify the impedance thereof, so that the assembly formed by the transducer and said tuning circuit has a determined resonant frequency.

16. The method according to claim 15, wherein the impedance modification of the tuning circuit is carried out by synchronous switching of a capacitor mounted in parallel with the transducer.

17. The method according to claim 15, wherein the switching of the capacitor and controlled by a feedback control relating to a detected phase difference between an input phase and an output phase, which are detected on the side of the input and respectively on the side of the output of an inductor mounted in series between the power interface and the transducer.

18. The method according to claim 15, the method further comprising controlling the ultrasonic transducers of the ultrasonic head by individually controlling one or more of amplitude, frequency, and phase of the drive signal of the supplying device that is configured to supply each of said ultrasonic transducers, to modify one or more of amplitude, frequency, and phase of the ultrasonic wave produced by each of said ultrasonic transducers.

19. The method according to claim 18, wherein modification of the one or more of amplitude, frequency, and phase of the ultrasonic wave produced by each of said ultrasonic transducers comprises modification of a focal point of said ultrasonic wave.

20. The method according to claim 15, wherein the determined resonant frequency is tuned to the setpoint frequency.

* * * * *